United States Patent
Yang et al.

(10) Patent No.: US 10,335,610 B2
(45) Date of Patent: Jul. 2, 2019

(54) CATHETER APPARATUS, BRACHYTHERAPY SYSTEM AND METHOD USING THE SAME

(71) Applicant: BRAXX BIOTECH CO., LTD, Taipei OT (TW)

(72) Inventors: Kai-Lin Yang, Taipei (TW);
Hsuan-Mien Wang, Taipei (TW);
Wei-Jer Chang, New Taipei (TW)

(73) Assignee: BRAXX BIOTECH CO., LTD, Taipei (TW)

(*) Notice: Subject to any disclaimer, the term of this patent is extended or adjusted under 35 U.S.C. 154(b) by 125 days.

(21) Appl. No.: 15/624,734

(22) Filed: Jun. 16, 2017

(65) Prior Publication Data
US 2017/0281969 A1    Oct. 5, 2017

Related U.S. Application Data

(63) Continuation-in-part of application No. PCT/CN2015/096832, filed on Dec. 9, 2015.

(30) Foreign Application Priority Data

Dec. 19, 2014  (CN) .......................... 2014 1 0798226

(51) Int. Cl.
*A61N 5/00*       (2006.01)
*A61N 5/10*       (2006.01)
*A61M 25/10*      (2013.01)

(52) U.S. Cl.
CPC ........... *A61N 5/1007* (2013.01); *A61M 25/10* (2013.01); *A61M 25/10185* (2013.11);
(Continued)

(58) Field of Classification Search
CPC ...... A61N 5/00; A61N 5/1001; A61N 5/1002; A61N 5/1007; A61N 5/1014; A61N 2005/1003; A61N 2005/1018
(Continued)

(56) References Cited

U.S. PATENT DOCUMENTS 6,527,692 B1 * 3/2003 Weinberger .......... A61N 5/1002
                                                   600/3
2006/0116546 A1  6/2006 Eng
(Continued)

FOREIGN PATENT DOCUMENTS

CN      2189938 Y     2/1995
CN    201342171 Y    11/2009
(Continued)

OTHER PUBLICATIONS

International Search Report of PCT Patent Application No. PCT/CN2015/096832 dated Feb. 3, 2016.

*Primary Examiner* — John P Lacyk

(57) ABSTRACT

The present application relates to a catheter apparatus including a tubular member, and four or more fluid-flow pipe members, each having a proximal end and a distal end, and each being disposed around a periphery of the tubular member along an axial direction thereof. Each of the four or more fluid-flow pipe members is provided with an independent positioning member at the distal end thereof, and the number of positioning members is four or more. A brachytherapy system and a method of reducing area of radiation exposure of normal tissue in a brachytherapy treatment using the catheter apparatus are also disclosed.

12 Claims, 4 Drawing Sheets

(52) U.S. Cl.
CPC ..... *A61N 5/1014* (2013.01); *A61M 2205/051* (2013.01); *A61N 5/1016* (2013.01)

(58) Field of Classification Search
USPC .......................................................... 600/1–8
See application file for complete search history.

(56) References Cited

U.S. PATENT DOCUMENTS

| | | |
|---|---|---|
| 2011/0034948 A1 | 2/2011 | Ravikumar |
| 2012/0078029 A1 | 3/2012 | Subramanian |
| 2013/0238038 A1 | 9/2013 | Auyoung |
| 2017/0028174 A1* | 2/2017 | Subramanian ....... A61N 5/1014 |
| 2017/0173362 A1* | 6/2017 | Lamoureux .......... A61N 5/1002 |

FOREIGN PATENT DOCUMENTS

| | | | |
|---|---|---|---|
| JP | H08173553 A | 7/1996 | |
| TW | 290464 B | 11/1996 | |

* cited by examiner

CATHETER APPARATUS, BRACHYTHERAPY SYSTEM AND METHOD USING THE SAME This patent application is a continuation-in-part application of International Application No. PCT/CN2015/096832 filed on Dec. 9, 2015, claiming priority from Chinese Patent Application No. 201410798226.0 filed on Dec. 19, 2014, the entire contents of which are incorporated herein by reference.

TECHNICAL FIELD

The present application relates to a catheter apparatus, and more specifically relates to a catheter apparatus for use in internal body cavities. The present application also relates to a brachytherapy system and method using the catheter apparatus.

BACKGROUND

Radiation therapy is a treatment for cancer which transmits radiation in the form of light waves or high-speed particles, using high-energy radiation to destroy cancer cells and inhibit their growth to achieve the purpose of treating cancer, and is commonly administered to patients who cannot tolerate surgery or for the treatment of recurrence after surgery.

Radiation therapy techniques are divided into two categories, one is teletherapy, and the other is brachytherapy. Teletherapy is an external radiotherapy which places the radioactive source outside the body. The generated beam of radiation passes through the body and make the treated area receive radiation exposure. Brachytherapy generates beam of radiation by the radioactive source in a catheter which is inserted into a body cavity and placed in the tumor tissue or near the surroundings of the tumor tissue to make the tumor receive radiation exposure to radiation to achieve the purpose of treatment.

Brachytherapy is suitable for treating tumors growing in a body cavity, and is widely used to treat cervical cancer, along with endometrial cancer, nasopharyngeal cancer, prostate cancer and other tumors that grow wherever a catheter can be placed.

Since the radioactivity is inversely proportional to the square of the distance from the source, when administrating brachytherapy, normal tissues or organs which are farther from the source are exposed to far less radiation than those in central areas. Such contrast can reduce radiation damage to normal tissues, and therefore the side effects caused by radiation therapy or the incidence of sequelae after radiation therapy can also be reduced.

Currently, brachytherapy instruments used in domestic market are mainly for high-dose rate brachytherapy, which shall be at the dose rate of more than 12-Gy/hour, while in Europe and in the United State, low-dose rate brachytherapy is more commonly used, and the dose rate shall be under 2-Gy/hour. Low-dose rate brachytherapy performs better biological properties than high-dose rate brachytherapy, since in a low-dose rate brachytherapy, the radiation damage the normal cells receive has a better chance to be repaired, and hence theoretically the incidence of sequelae is lower than the latter.

However, when comparing to the low-dose brachytherapy, the high-dose rate brachytherapy has many advantages: (1) less expensive, patients can be treated as outpatients without hospitalization for days; (2) the treatment time is short and therefore it is more comfortable for patients; (3) the treatment time is short, so the positional stability of the source which is temporarily placed in the body is higher; (4) radiation therapy practitioners do not have the concern of unnecessary radiation dose exposure.

Nevertheless, when brachytherapy is administered, it also causes damages to the exposed normal tissues surrounding the tumor, and the occurrence of the side effects of radiation therapy is exactly related to the exposed area and dose. Hence, the closer to the source the normal tissues are, the higher dose they receive, and the greater the side effect is.

Generally side effects of radiation therapy are fatigue, skin redness and fragile skin of radiation area. Body parts which are rubbed frequently such as armpit and groin etc., are prone to inflammation and scratch. Abdominal radiotherapy often causes diarrhea as a side effect.

Radiation therapy to the head and neck may cause thick saliva, low saliva production, altered taste, redness of the oral mucosa, dry mouth, dysphagia and painful swallowing, even loss of appetite and so on.

On the other hand, since the radiation therapy is administered by inserting a catheter into the body cavity to treat the surrounding tumor tissues. A conventional catheter, such as an Elekta's Bonvoisin-Gerard Esophageal Applicator product, is placed in a body cavity and the whole section of the catheter is inflated to keep the cavity open. This helps the delivery of a radioactive source. However, the way that inflating the whole section of the catheter to keep the cavity open causes discomfort to patients during treatment.

Therefore, designing an apparatus which abates the patients' discomfort caused by the administration of radiation therapy, and decreasing the scope of normal tissue exposure to reduce side effects from the treatment, is really an issue remains to be solved currently.

SUMMARY

According to one aspect, there is provided a catheter apparatus, including a tubular member; and four or more fluid-flow pipe members, each having a proximal end and a distal end, and each being disposed around a periphery of the tubular member along an axial direction thereof; wherein each of the four or more fluid-flow pipe members is provided with an independent positioning member at the distal end thereof, and wherein four or more positioning members are provided.

According to one embodiment, each of the four or more fluid-flow pipe members is further provided with an independent control element at the proximal end thereof, and the control element couples with the positioning member through the fluid-flow pipe member.

According to one embodiment, each of the four or more fluid-flow pipe members is further provided with a valve device at the distal end thereof.

According to one embodiment, at least four of the fluid-flow pipe members have different lengths, such that the positioning members coupling with their respective fluid-flow pipe members are arranged one behind another along the axial direction of the tubular member.

According to one embodiment, an outer tube member is provided outside the tubular member and the fluid-flow pipe members, the outer tube member being integrally formed and having an internal space to accommodate the tubular member and the fluid-flow pipe members, and wherein the tubular member is situated in a center of the outer tube member and the positioning members.

According to one embodiment, the outer tube member includes an inner wall surface and an outer wall surface: wherein the fluid-flow pipe members pierce through the outer tube member from an inner wall surface to an outer wall surface to couple with their respective independent positioning members.

According to one embodiment, the outer tube member forms a sealed blind end at the distal ends.

According to one embodiment, the control elements adjust a size of their respective coupled positioning members.

According to one embodiment, each of the positioning members is a cylindrical member surrounding the tubular member, wherein the positioning members are equidistantly spaced apart.

According to one embodiment, each positioning member is an inflatable and deflatable member.

According to another aspect, there is provided a brachytherapy system, including a brachytherapy instrument; a catheter apparatus, as disclose in the present application, connected to the brachytherapy instrument; and a radioactive source released from the brachytherapy instrument and stayed in the tubular member of the catheter apparatus.

According to one embodiment, the radioactive source is capable of being moved inside the tubular member, and staying in a middle of one of the positioning members or between two of the positioning members.

According to yet another aspect, there is provided a method of reducing area of radiation exposure of normal tissue in a brachytherapy treatment, including the steps of: applying a brachytherapy system as disclosed in the present application; using the independent control elements to inflate the four or more positioning members to different extents of inflation so as to make the catheter apparatus conformable to the body cavity; and releasing the radioactive source from the brachytherapy instrument into the tubular member of the catheter apparatus.

The catheter apparatus of the present application applies four or more fluid-flow pipe members and each of them having an independent positioning member so that the catheter apparatus can be placed in the body cavity more conformable to the tissue and shape of the body cavity to reduce discomfort caused by keeping the body cavity open, and eliminate side effects because of its better conformity.

DETAILED DESCRIPTION

Unless otherwise defined, all technical and scientific terms in the context represent the same meanings which a person having ordinary skill in the art comprehends with.

The term "fluid-flow pipe" used in the present application refers to a tube that fluid, for instance air, can be infused from its proximal end so that a fluid, such as air, can pass through the fluid-flow pipe and reach a positioning member at its distal end.

The term "positioning member" used in the present application refers to a structure that can conduce to the stability of the position of the catheter apparatus in a body cavity. A preferred structure of the positioning member is a balloon structure.

The term "axial direction" used in the present application refers to the direction of a longitudinal axis of a tubular member extending longitudinally at the center of a catheter apparatus.

The term "control element" used in the present application refers to the element provided at the proximal end of the fluid-flow pipe which is able to control the size of the positioning member at the distal end of the fluid-flow pipe such that the positioning member can have the capability to fix the position of the catheter apparatus in a body cavity.

The catheter apparatus of the present application can allow people skilled in the art to understand the spirit of creation and make the catheter apparatus according to the following description of the embodiments. The enforcement pattern of the present application is not limited by the embodiments.

An embodiment of the catheter apparatus of the present application may include a tubular member and four or more fluid-flow pipe members, each having a proximal end and a distal end, and each being disposed around a periphery of the tubular member along an axial direction thereof. Each of the four or more fluid-flow pipe members may be provided with an independent positioning member at the distal end thereof, and the number of positioning members is four or more. Each of the four or more fluid-flow pipe members may be further provided with an independent control element at the proximal end thereof, and the control element couples with the positioning member through the fluid-flow pipe member. The catheter apparatus of the embodiment in the present application may further include an outer tube member.

Figure 1:
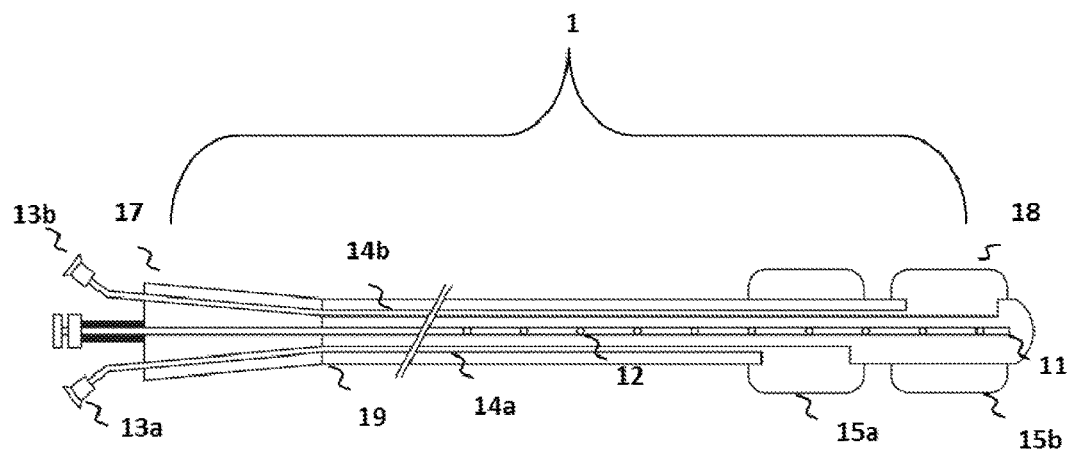
FIG. 1 is a schematic side view of a catheter apparatus according to an embodiment of the present application.

As shown in FIG. 1, the catheter apparatus 1 may include a tubular member 11; an outer tube member 19; fluid-flow pipes 14a, 14b; control elements 13a, 13b; and positioning members 15a, 15b. The tubular member 11 can be configured to receive a radioactive source 12. The control element 13a can control a fluid (not shown) as a valve device to enter the fluid-flow pipe 14a and inflate the positioning member 15a at the distal end 18. Since the positioning member 15b, which couples with the fluid-flow pipe 14b and the control element 13b, is independent from the fluid-flow pipe 14a and the control element 13a coupled with the positioning member 15a, the positioning member 15a and the positioning member 15b can have different extents of inflation according to demands, which results in the capability of controlling the sizes of the positioning members respectively.

The outer tube member 19 may be integrally formed, and may have an internal space to accommodate the tubular member 11 and the fluid-flow pipe members 14a and 14b. The tubular member 11 may be situated in the center of the outer tube member 19 and the positioning members 15a, 15b.

Figure 2:
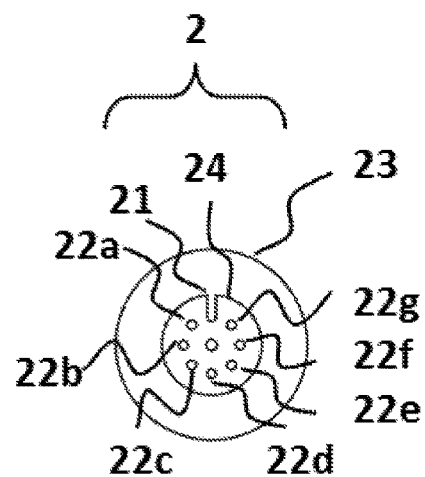
FIG. 2 is a cross-sectional view of the catheter apparatus according to an embodiment of the present application.

FIG. 2 is a cross-section of an embodiment of the catheter apparatus 2 in the present application. The fluid-flow pipe 21 can pierce through the outer tube member 19 from an inner wall surface to an outer wall surface so as to couple with the independent positioning member 23. Other fluid-flow pipes 22a, 22b, 22c, 22d, 22e, 22f and 22g coupling to the positioning members may differ in length among each other, and hence they can pierce through the outer tube member 24 at different locations of cross-section so as to couple with their respective positioning members.

Figure 3:
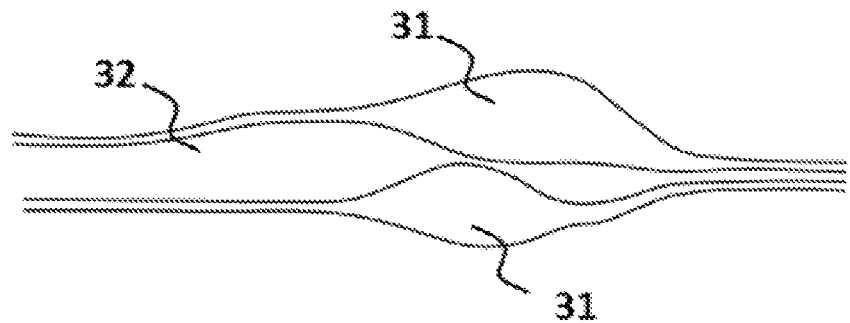
FIG. 3 is an illustrative diagram showing tumor tissues in a body cavity.

FIG. 3 is an illustrative diagram of tumor tissues 31 in a body cavity 32. As shown in FIG. 3, the inner space of the body cavity 32 has irregular shape changes due to the existing of the tumor tissues 31 which results in the risks of incapability of using medical devices smoothly in the body cavity or accidental injury to peripheral tissues.

Figure 4:
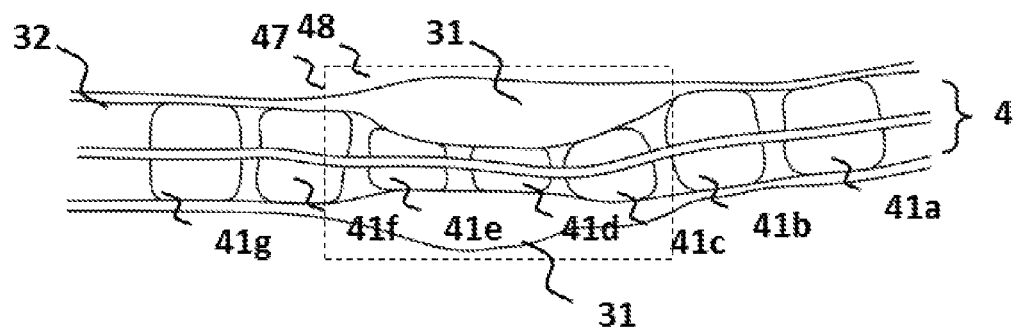
FIG. 4 is an illustrative diagram showing the catheter apparatus being placed in the body cavity with tumor tissues.
Figure 5:
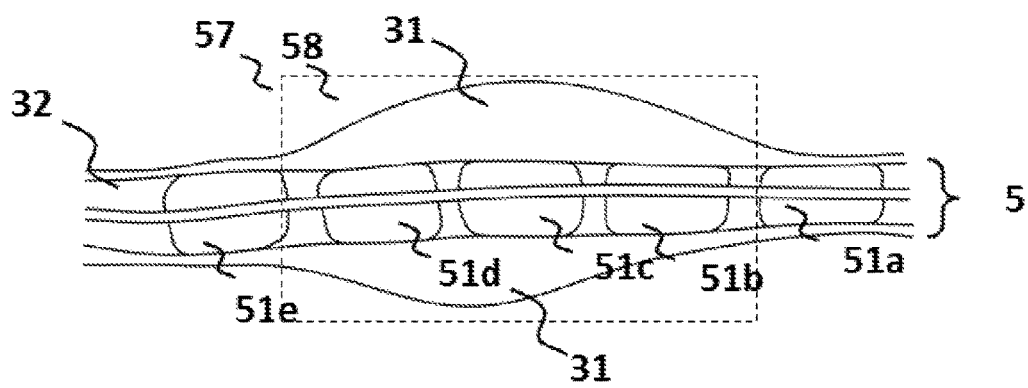
FIG. 5 is an illustrative diagram showing a catheter apparatus of the prior art being placed in the body cavity with tumor tissues.

As shown in FIG. 4, the catheter apparatus 4 may include fluid-flow pipes (not shown) and the positioning members 41a, 41b, 41c, 41d, 41e, 41f and 41g. In this embodiment, the lengths of the space between adjacent positioning members are equal, i.e. the positioning members are equidistantly spaced apart. According to the embodiment of the present application, when the catheter apparatus 4 enters the body cavity 32, the positioning members 41a, 41b, 41c, 41d, 41e, 41f and 41g can have different extents of inflation, so that the catheter apparatus 4 can conform to the shape of the tumor tissues 31, and hence can be stable in the body cavity 32. In FIG. 4, the dotted line indicates the area of radiation exposure 47. The area of radiation exposure 47 covers the tumor tissues 31 and the peripheral normal tissue 48. Comparing to the existing catheter apparatus 5 in FIG. 5, since the existing catheter apparatus 5 does not have the features of the embodiments of the present application and is unable to respectively control the extents of inflation of positioning members 51a, 51b, 51c, 51d and 51e, the positioning members 51a, 51b, 51c, 51d and 51e have the same extent of inflation. In order to cover the whole tumor tissues 31, the peripheral normal tissue 58, which is covered by the area of radiation exposure 57, is larger than the peripheral normal tissue 48 in FIG. 4. By the above comparison, it can be understood that the catheter apparatus 4 of the embodiment in the present application can result in smaller peripheral normal tissue 48 and thus the side effects can be reduced. Furthermore, since the existing catheter apparatus 5 is hard to conform in shape with the tumor tissues 31 while keeping the body cavity open, it causes discomfort to the patients. By contrast, it can be understood that the catheter apparatus which has the features of the embodiments in the present application can help to solve the problems of existing prior art.

Figure 6:
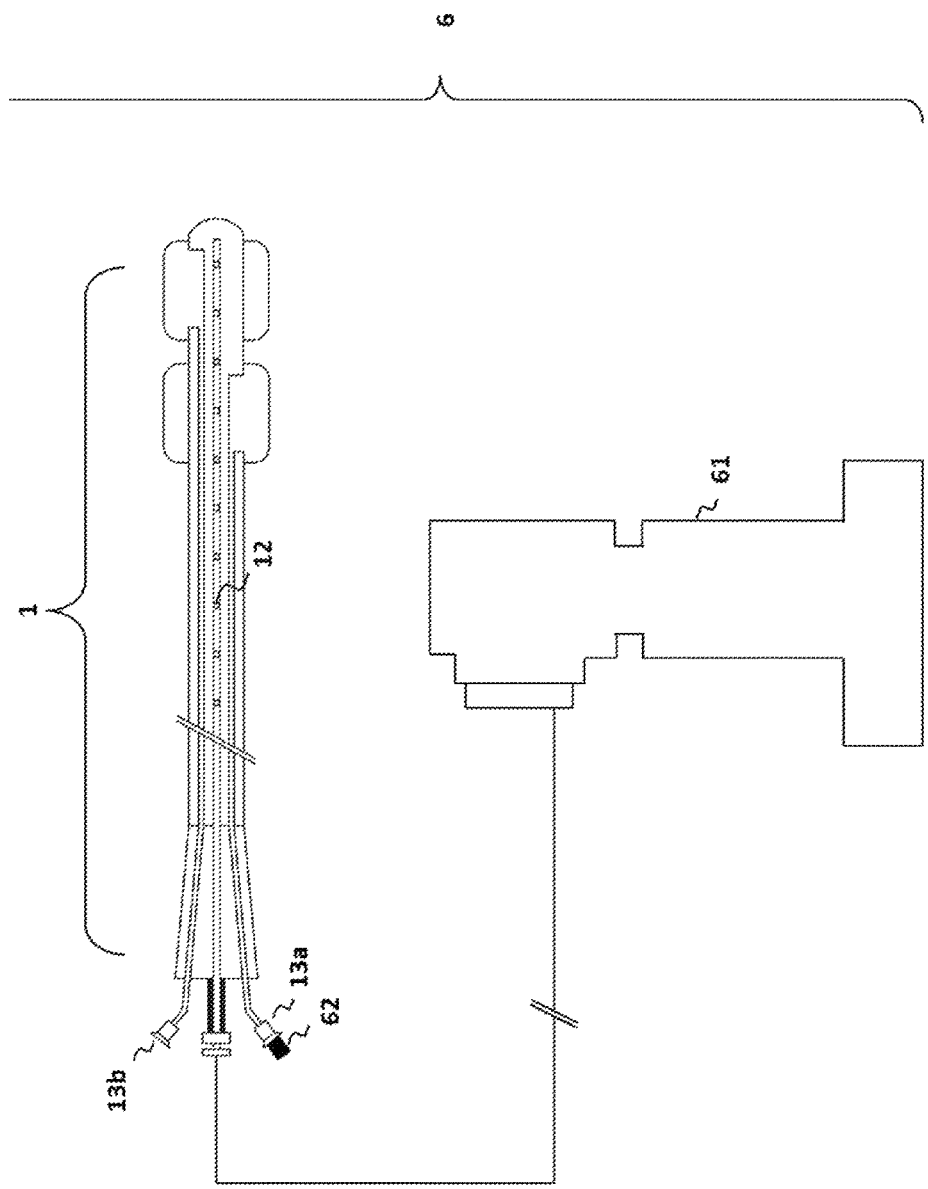
FIG. 6 is a schematic side view of a brachytherapy system according to an embodiment of the present application.

As shown in FIG. 6, when administering brachytherapy treatment, the catheter apparatus 1 in the present application can be used together with a brachytherapy instrument 61 to form a brachytherapy system 6. The catheter apparatus 1 can be connected to the brachytherapy instrument 61 where a radioactive source 12 can be released from the brachytherapy instrument 61 into the tubular member 11 of the catheter apparatus 1. The radioactive source 12 can be moved inside the tubular member 11 and can stay in the middle of one of the positioning members 51a, 51b, 51c, 51d and 51e or between two of the positioning members 51a, 51b, 51c, 51d and 51e, according to the needs. In addition, the control elements 13a, 13b can choose whether be connected to a valve device 62 or not.

The present application also provides a method of reducing the area of radiation exposure of normal tissue in a brachytherapy treatment. The method may include the steps of: applying a brachytherapy system 6 as disclosed in the present application; using the independent control elements to inflate the four or more positioning members 51a, 51b, 51c, 51d and 51e to different extents of inflation so as to make the catheter apparatus conformable to the body cavity; and releasing the radiation source from the brachytherapy instrument 61 into the tubular member 11 of the catheter apparatus.

The present application provide a catheter, a brachytherapy system 6 and a method to reduce discomfort to patients and reduce the area of radiation exposure to the peripheral normal tissue. The description of the catheter of the embodiment in the present application is about administering radiation source to treat a tumor.

However, the usages of the catheter of the present application are not limited to treat tumor tissues. In any treatments which need catheters to keep the body cavity open, the technical features disclosed in the present application can be applied to make the catheter more conformable when entering the body cavity, thereby reducing discomfort to the users and achieving better results.

What is claimed is:

1. A catheter apparatus, comprising:
a tubular member; and
four or more fluid-flow pipe members, each having a proximal end and a distal end, and each being disposed around a periphery of the tubular member along an axial direction thereof;
wherein each of the four or more fluid-flow pipe members is provided with an independent positioning member at the distal end thereof; and wherein four or more positioning members are provided;
an outer tube member is provided outside the tubular member and the fluid-flow pipe members, and the outer tube member forms a sealed blind end at the distal ends; and
the four or more fluid-flow pipe members pierce through the outer tube member from an inner wall surface of the outer tube member to an outer wall surface thereof at different locations of the outer tube member so as to couple with respective positioning members.

2. The catheter apparatus according to claim 1, wherein each of the four or more fluid-flow pipe members is further provided with an independent control element at the proximal end thereof, and the control element couples with the positioning member through the fluid-flow pipe member; when the catheter apparatus enters a body cavity, the four or more positioning members are controlled to have different extents of inflation, so that the catheter apparatus conforms to a shape of a tumor tissue in the body cavity.

3. The catheter apparatus according to claim 1, wherein each of the four or more fluid-flow pipe members is further provided with a valve device at the distal end thereof.

4. The catheter apparatus according to claim 2, wherein at least four of the fluid-flow pipe members have different lengths, such that the positioning members coupling with their respective fluid-flow pipe members are arranged one behind another along the axial direction of the tubular member.

5. The catheter apparatus according to claim 4, wherein the outer tube member is integrally formed and has an internal space to accommodate the tubular member and the fluid-flow pipe members, and wherein the tubular member is situated in a center of the outer tube member and the positioning members.

6. The catheter apparatus according to claim 5, wherein the outer tube member comprises an inner wall surface and an outer wall surface; wherein the fluid-flow pipe members pierce through the outer tube member from the inner wall surface to the outer wall surface to couple with their respective independent positioning members.

7. The catheter apparatus according to claim 6, wherein the control elements adjust a size of their respective coupled positioning members.

8. The catheter apparatus according to claim 7, wherein each of the positioning members is a cylindrical member surrounding the tubular member, and wherein the positioning members are equidistantly spaced apart.

9. The catheter apparatus according to claim 1, wherein each positioning member is an inflatable and deflatable member.

10. A brachytherapy system, comprising:
a brachytherapy instrument;
a catheter apparatus, as claimed in claim 2, connected to the brachytherapy instrument; and
a radioactive source released from the brachytherapy instrument and stayed in the tubular member of the catheter apparatus.

11. The brachytherapy system according to claim 10, wherein the radioactive source is capable of being moved inside the tubular member and staying in a middle of one of the positioning members or between two of the positioning members.

12. A method of reducing area of radiation exposure of normal tissue in a brachytherapy treatment, comprising:
applying a brachytherapy system, as claimed in claim 10;
using the independent control elements to inflate the four or more positioning members to different extents of inflation so as to make the catheter apparatus conformable to a body cavity; and
releasing the radioactive source from the brachytherapy instrument into the tubular member of the catheter apparatus.

* * * * *